United States Patent
Pike et al.

[11] Patent Number: 6,122,045
[45] Date of Patent: *Sep. 19, 2000

[54] APPARATUS AND METHOD FOR VIEWING AND INSPECTING A CIRCUMFERENTIAL SURFACE AREA OF AN OBJECT

[75] Inventors: John Nazarian Pike, Pleasantville, N.Y.; Yogesh Mehrotra, Monroe; Herbert Kaplan, Norwalk, both of Conn.

[73] Assignee: Materials Technologies Corporation, Monroe, Conn.

[ * ] Notice: This patent is subject to a terminal disclaimer.

[21] Appl. No.: 09/326,957

[22] Filed: Jun. 7, 1999

Related U.S. Application Data

[63] Continuation-in-part of application No. 08/959,387, Oct. 28, 1997, Pat. No. 5,936,725.

[51] Int. Cl.[7] ............................. G01N 21/88; G02B 23/24
[52] U.S. Cl. ........................ 356/237.1; 348/125; 259/798
[58] Field of Search ........................ 356/237.1, 384–387, 356/241; 348/125; 359/402, 403, 725, 726, 860, 866, 918, 927, 798

[56] References Cited

U.S. PATENT DOCUMENTS

| | | | |
|---|---|---|---|
| 3,515,475 | 6/1970 | Zukor | 353/78 |
| 3,836,261 | 9/1974 | Clarke | 356/200 |
| 3,884,577 | 5/1975 | Carpentier et al. | 355/77 |
| 4,025,198 | 5/1977 | Hutchins | 356/163 |
| 4,326,808 | 4/1982 | Pryor et al. | 356/445 |
| 4,358,202 | 11/1982 | Puffer et al. | 356/430 |
| 4,561,778 | 12/1985 | Kleinhuber | 356/387 |
| 5,061,074 | 10/1991 | Ohikata | 356/390 |
| 5,126,872 | 6/1992 | Birkle | 356/385 |
| 5,278,632 | 1/1994 | Shotwell | 356/376 |
| 5,661,294 | 8/1997 | Buchmann | 250/223 |
| 5,936,725 | 8/1999 | Pike et al. | 356/237.1 |

*Primary Examiner*—Hoa Q. Pham
*Attorney, Agent, or Firm*—Cummings & Lockwood

[57] ABSTRACT

An apparatus (10) and method is provided for generating a 360° view of a surface area of a three-dimensional object, such as a wire or cable, and for inspecting the surface area for flaws or imperfections. A receiving lens (12) defines an optical axis (14) extending through the object, and an origin (0) located on the optical axis within the object and spaced a predetermined distance (S) from the receiving lens (12), for generating a direct image of a front surface section of the object. A first mirror (16) is spaced a first predetermined distance (L1) from the origin (0) on another side of the object relative to the receiving lens (12) for generating a first mirror image of a first rear surface section of the object. A second mirror (18) is spaced a second predetermined distance (L2) from the origin (0) on another side of the object relative to the receiving lens (12), and on another side of the optical axis (14) relative to the first mirror, for generating a second mirror image of a second rear surface section of the object. The first and second mirror images are each defined in part by a first and second central ray (18, 22), respectively, and each central ray forms an angle of incidence (θ1, θ2) on the respective mirror. The first and second predetermined distances (L1, L2) and the angles of incidence (θ1, θ2) of the mirrors are each selected to simultaneously generate at least three spatially distinct, non-vignetting images forming a 360° view of the surface area.

20 Claims, 8 Drawing Sheets

FIG. 15

APPARATUS AND METHOD FOR VIEWING AND INSPECTING A CIRCUMFERENTIAL SURFACE AREA OF AN OBJECT

CROSS-REFERENCE TO RELATED APPLICATION

This patent application is a continuation-in-part of U.S. patent application Ser. No. 08/959,387, filed Oct. 28, 1997, now U.S. Pat. No. 5,936,725 entitled "Apparatus And Method For Viewing And Inspecting A Circumferential Surface Area Of A Test Object", herewith, and which is hereby expressly incorporated by reference as part of the present disclosure.

FIELD OF THE INVENTION

The present invention relates to apparatus and methods for viewing and inspecting a 360° or circumferential surface section of a three-dimensional test object, such as a cylindrical, square or elliptical wire or cable having an insulative coating or polymeric layer thereon, and more particularly, to an apparatus and method for simultaneously viewing a 360° or circumferential surface area of a test object and generating a plurality of distinct surface images, wherein each surface image covers a respective portion of the circumferential surface area, and is spatially separated, substantially without vignetting, from the other surface images.

BACKGROUND INFORMATION

The detection of surface flaws in wires, cables, and like three-dimensional objects is frequently accomplished by visual/manual inspection. For example, the detection of such flaws or imperfections in polymeric coatings or insulative layers on wires and cables (such as stress cracks (from the external surface inward) and abrasion chipping) is presently accomplished by close visual inspection. For such surface or surface-inward flaws, visual imaging is frequently sufficient for predicting the effective future service life of the wire/cable or its insulation. However, in direct visual inspection, the inspector can see only at the most one-half the circumference of the insulated wire. To see the hidden part of the circumference, the inspector either must physically rotate the wire or relocate himself with respect to the wire. Frequently, rotation of the wire will unnecessarily stress either the wire or its insulative layer. In other instances, the wire is fixedly secured or attached to another structure, such as an interior wall or surface, including that of an aircraft or other vehicle, thus preventing the inspector from relocating himself to view the hidden portion of the wire.

Accordingly, it is an object of the present invention to overcome the drawbacks and disadvantages of prior art apparatus and methods for visual and/or camera inspection of the surface structure and/or integrity of a test object, and to provide a novel apparatus and method for viewing all sides (or 360°) of a test surface, such as the circumferential surface of a wire or cable, to thereby increase overall inspection speed, reliability and/or thoroughness.

SUMMARY OF THE INVENTION

The present invention is directed to an apparatus and method for generating a 360° view of a target surface of a three-dimensional object, examples of which include a wire or cable that may or may not have an insulative layer thereon, and for visually or otherwise inspecting the target surface for flaws or imperfections. The apparatus comprises a receiving lens defining an optical axis extending through the object, and an origin located on the optical axis within the object and spaced a predetermined distance from the receiving lens, for generating a direct image of a front surface section of the object. A first mirror is spaced a first predetermined distance from the origin on an opposite side of the object relative to the receiving lens, and the first mirror generates a first mirror image of a first rear surface section of the object. A second mirror is spaced a second predetermined distance from the origin on an opposite side of the object relative to the receiving lens, and on an opposite side of the optical axis relative to the first mirror, and the second mirror generates a second mirror image of a second rear surface section of the object. The first and second mirror images are each defined in part by a first and second central ray, respectively (i.e., a ray extending from the origin or center of the test object to the respective mirror), and each central ray defines a respective angle of incidence with respect to the first or second mirror. In accordance with the invention, the first and second predetermined distances and the first and second angles of incidence of the mirrors may be selected to generate at least three distinct, non-vignetting images forming a 360° view of the target surface of the object. The images themselves may be formed by reflected or emitted UV, visible, or infrared radiation from the test object.

Accordingly, one advantage of the apparatus and method of the invention is that an inspector, camera or other viewing device may simultaneously view all sides of a wire, cable or other three-dimensional test object. In addition, the inspector and/or camera may simultaneously view at least three images, separated spatially, and substantially without vignetting between images. Yet another advantage of the present invention is that the same mirror configuration and associated method of viewing may be employed for both UV and infrared inspection and viewing.

Other objects and advantages of the present invention will become apparent in view of the following detailed description and accompanying drawings.

DETAILED DESCRIPTION OF THE PREFERRED EMBODIMENTS

Figure 1:
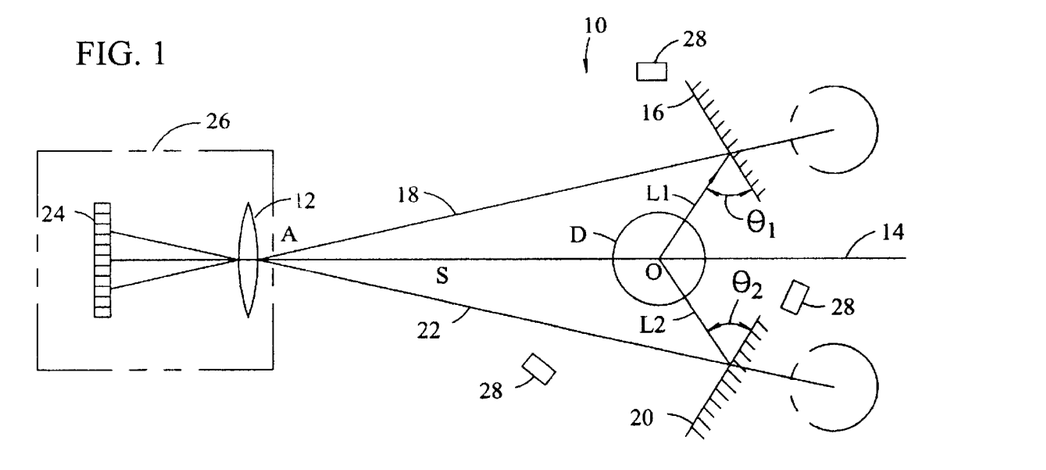
FIG. 1 is a schematic view of a first embodiment of the invention employing a double-mirror configuration for simultaneously viewing all sides of a cable, wire or other test object.

In FIG. 1, an apparatus embodying the present invention for generating a 360° view of a target surface area of a test object and for visually or otherwise inspecting the target surface, is indicated generally by the reference numeral 10. The test object illustrated in FIG. 1 is a wire or cable defining an outer diameter "D". However, as will be recognized by those skilled in the pertinent art, the apparatus and method of the present invention equally may be employed to generate a 360° view of any of numerous objects, defining any of numerous configurations, such as a square, elliptical or other unique cross-sectional configuration, and/or may be employed to simultaneously view several test objects, such as a bundle of wires or cables, or other aggregates.

The apparatus 10 comprises a receiving lens 12 defining an optical axis 14 extending through the test object, and an origin "O" located on the optical axis within the test object. In the embodiment of the present invention illustrated, the origin "O" is located at the center of the test wire or cable (defining a circular cross-sectional configuration). As can be seen, the receiving lens 12 receives and generates a first direct, two-dimensional image of a front surface section of the test object.

The apparatus 10 further comprises a first mirror 16 spaced a first predetermined distance "L1" from the origin "O" on an opposite side of the test object relative to the receiving lens 12. As shown in broken lines in FIG. 1, the first mirror 16 generates a first two-dimensional reflected image of the first mirror's field of view corresponding to a first rear surface section of the test object. As also shown in FIG. 1, the first reflected image is defined in part by a first central or chief ray 18 defining a first angle of incidence "θ1" upon the first mirror 16. The first central ray 18 is the one traveling along the line extending between the origin "O" (or center of the test object) and the first mirror 16, which is received by the receiving lens 12 at the center point "A" located on the optical axis 14.

A second mirror 20 is spaced a second predetermined distance "L2" from the origin "O" on an opposite side of the test object relative to the receiving lens 12, and on an opposite side of the optical axis 14 relative to the first mirror 16. As shown in broken lines in FIG. 1, the second mirror 18 generates a second two-dimensional reflected image of the second mirror's field of view corresponding to a second rear surface section of the test object. The second reflected image is defined in part by a second central or chief ray 22 defining a second angle of incidence "θ2" upon the second mirror 20. The second chief ray 22 is the one traveling along a line extending between the origin "O" (or center of the test object) and the second mirror 20, and which is received by the receiving lens 12 at the center point "A" located on the optical axis 14. The mirrors 16 and 20 are preferably front surface, planar mirrors positioned so that the three or more images of the test surface will simultaneously appear side-by-side upon transmission through the receiving lens 12. As will be recognized by those skilled in the pertinent art, the receiving lens 12 may be defined in the most basic case by an inspector's eye lens, but is preferably defined by a viewing device, such as a visual or infrared ("IR") camera having planar detector mosaics for visually displaying the viewed images in the preferred side-by-side manner.

The use of front surface mirrors 16 and 20 ensures that the radiant energy emitted or reflected by the target surface and sensed by a camera or eye is not spectrally limited, but can be any wavelength region of interest from the ultraviolet ("UV") through the visible to the far-IR. However, if visible inspection only is desired, conventional rear surface mirrors may be employed instead. In addition, curved mirrors rather than plane mirrors also may be employed. When appropriately configured, curved mirrors may produce a more normalized view and/or a more uniform irradiation of the target surface.

As also shown in FIG. 1, a detector 24 is optically coupled to the receiving lens 12 for receiving the direct image of the front surface section, and as shown in broken lines in FIG. 1, the receiving lens and detector preferably form components of a viewing camera 26. As is described further below, the first and second reflected images of the two rear surface sections of the target surface are preferably displayed on an image screen of the viewing camera in a side-by-side relationship. For ease of viewing, the apparatus 10 preferably further comprises three sub-miniature lamps 28, which are spaced approximately 120° apart, and positioned to illuminate from the side the viewed region of the test surface. In addition, the sub-miniature lamps 28 are preferably blocked from direct and mirror views to avoid visual glare at the observation point of the eye or camera lens.

As is described further below, the choice and placement of the mirrors 16 and 20 are preferably designed so that every point on the circumference of the target surface under inspection appears in at least one of the images falling simultaneously on the detector mosaic. In addition, as is described further below, the same mirror configuration can be utilized both for irradiating and viewing all sides of the test object simultaneously, in any wavelength region from UV through IR, by adding one or several lamps or laser components to the basic viewing configuration of FIG. 1.

In accordance with the present invention, the first and second predetermined distances L1 and L2, respectively, and the first and second angles of incidence of the mirrors θ1 and θ2, respectively (or the angular orientations of the first and second mirrors 16 and 20, respectively), are each selected to generate at least three distinct, non-vignetting images forming a 360° view of the surface area of the test object under inspection, and visually arranged in a side-by-side manner. These features of the present invention are particularly advantageous if quantitative mapping or quantitative thermography of the target surface is desired. A further advantage of the preferred embodiment of the invention (which is also consistent with the condition of non-vignetting images) is that the mirrors of the apparatus may be configured so that all three views simultaneously seen from three directions are equiangular and symmetrically spaced around the circumference (or perimeter) of the test object. This feature significantly eases the software requirements for quantitative surface mapping and/or thermography.

In order to generate three equiangular views of the test surface, lines L1 and L2 of the first and second chief rays should each be inclined at approximately ±60° with respect to the optical axis 14 (i.e., the first and second angles of incidence θ1 and θ2, respectively, are each approximately ±60°), and the mirrors are configured with respect to the receiving lens 12 so that the chief rays eventually pass through the center point A of the lens. To generate the non-vignetting images, the length of each of the lines L1 and L2 must be greater than or equal to a minimum value which is determined in a manner known to those of ordinary skill in the pertinent art based on the distance "S" between the receiving lens 12 and the origin "0", the diameter D of the test object (or, if not circular, another major cross-sectional dimension) and the diameter of the receiving lens 12. In the embodiment of FIG. 1, "non-vignetting" is used in a relatively restricted sense: L1 and L2 must be of sufficient length that all parts of the upper and lower reflected images can be seen from every point on the surface of the receiving lens 12. When viewing is by means of an infrared-sensitive camera, as is described further below, adherence to this condition is required for thermal images of the circumference of the object to represent true temperatures. Analysis shows that minimum L1 and L2 are uniquely determined in terms of S, D, and the receiving lens diameter when the chief or central rays emanate at ±60° from the origin "0". In addition, since all the relevant optomechanical parameters are thus either known or can be computed for any receiving lens or test object size, a computer program can be used, if desired, to determine the positioning and tilt of either mirror 16 or 20.

It is noted that for configurations where the distance "S" is relatively large, the tilt of each mirror 16 and 20 with respect to the optical axis 14 should be one or several degrees under 60° (and thus the preferred tilt is defined herein as "approximately ±60°"). In addition, as will be recognized by those skilled in the pertinent art, the first and second predetermined distances L1 and L2, respectively, can be any convenient distance larger than the minimum distance necessary to prevent vignetting, and generally limited only by the necessity to keep all three images of the test object within the extent of a film frame or the mosaic detector of a viewing camera.

Figure 2:
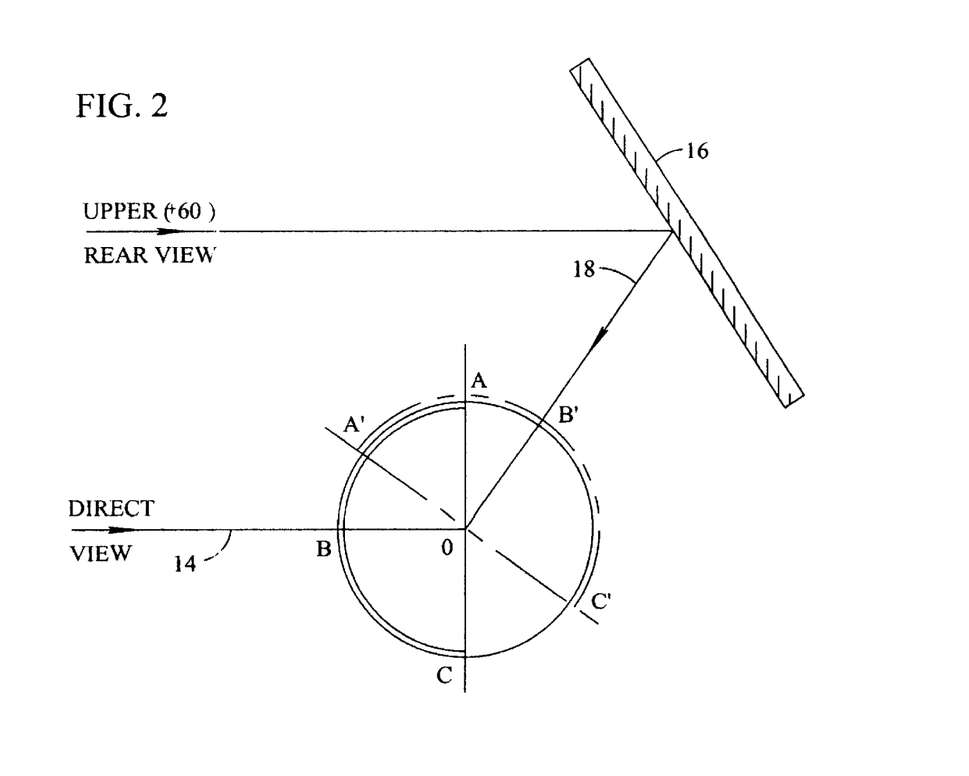
FIG. 2 is a schematic view of the first or upper-rear mirror of the apparatus of FIG. 1 and illustrating the manner in which the apparatus and method of the invention may be configured to provide areas of image overlap or redundancy.

In the preferred embodiment of the invention, each of the mirror views shows its particular one-half of the circumference of the wire or other test object. Thus, the "direct," "upper" and "lower" views provide a significant degree of imaging redundancy, and more than sufficient visual information for the inspector to be certain that all points along the circumference are viewed simultaneously. As shown typically in FIG. 2, in the direct view the inspector sees the side of the test surface described by the 180° solid arc ABC. In the upper reflected view of the mirror 16, the inspector sees the 180° dashed arc A'B'C'. With the direction of the first chief ray 18 set at 60°, as described above, the redundant visual overlap view is the 60° arc A'A. Thus, a surface flaw, crack or other imperfection located anywhere in the arc A'A will be seen simultaneously in both the direct and upper views of the target surface. Introduction of the second mirror 20 at -60° to the optical axis as shown in FIG. 1 creates two additional 60° overlap arcs of redundant imagery, all visible to the inspector. As will be recognized by those skilled in the pertinent art, if the inspector's eye is replaced by a television or like visual camera, with image signals transmitted to appropriate software, the redundancy of image information in the three overlap arcs (after correction for the mirror inversions of the images) can be used to produce a precise circumferential mapping of observed surface flaws. In addition, the presence of the three regions or arcs of image overlap provides internal dimensional calibration for all three views. Unless otherwise stated, the term "inspector" is used herein to describe either a person or viewing device, such as a television or IR camera.

As described in further detail below, the apparatus of the invention may be mounted within a hand-held instrument configured much like a soldering or caulking gun. The first and second mirrors 16 and 20 may be mounted in a pair of upper and lower jaws, respectively, and a spring-loaded trigger may be connected to one or both jaws to open and close them. In the operation of the instrument, the trigger is depressed to open the jaws and receive the wire or like test object over the origin "0" of the instrument, and the trigger may then be released to close the jaws around the test object without necessarily contacting the object. The instrument then may be moved slowly by hand (i.e., "scanned") along the wire or other test object until an obstruction prevents further travel or the entire object is scanned. Thus, the hand-held instrument permits the inspector to see all parts of the wire insulation surface (or other test surface) along the entire unobstructed length of the test object in an uninterrupted sequential view.

During such a "scan", the inspector may wish to move the instrument slightly toward and away from the wire target, to obtain the sharpest possible imagery at will at any point of interest on the target surface. The inspector's normal hand-eye coordination will tend automatically to do this in any case, similar to what one does naturally when reading at normal reading distances: the depth of field of the normal eye is more than sufficient to keep this "hunting" for best focus to an unnoticeable minimum.

For television or like camera viewing using low f/number lenses, the images from the mirrors appear farther from the receiving lens than does the direct image, and therefore hunting for the best focus may present further difficulties. A preferred practical solution is to focus the camera at the mid-point between the two distances, and to increase the f/number of the lens to such a value that the resolution blur circles of both direct and mirror images are within the resolution of the CCD image receptor of the camera. With this compromise (which may entail increased illumination of the test surface), the inspector will not have to "hunt" for the best image.

Figure 3:
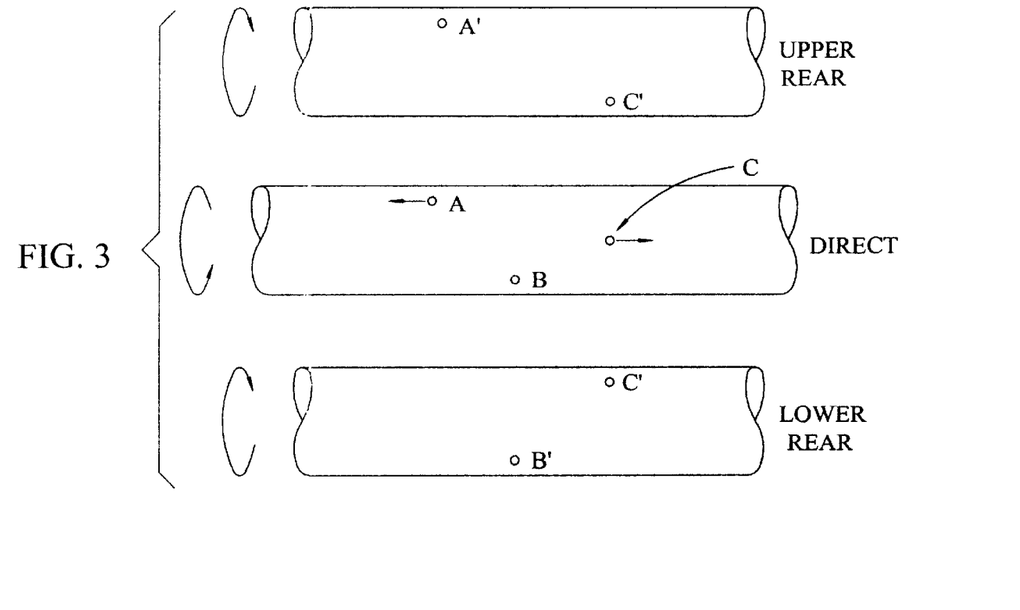
FIG. 3 is a schematic illustration of the three, side-by-side images ("upper rear", "direct" and "lower rear") generated by the apparatus of FIG. 1.

Turning to FIG. 3, typical "direct", "upper rear", and "lower rear" views generated and arranged in a side-by-side manner in accordance with the invention are illustrated schematically. Because of the laws of plane mirror reflection, each of the reflected rear views is inverted with respect to the direct view. The actual test or target surface is seen in the direct view: spots A and B are shown on the directly visible portion of the test surface (selected here to be within the overlap arc regions of the surface), and there is assumed to be a third spot C in the middle of the rear (hidden) side of the test surface. The upper and lower rear views, which the inspector also sees, show where the reflections of the points A, B and C are located: at A', B' and C'. This emphasizes the advantages described above with reference to FIG. 2, that any flaw or spot in one of the three overlap arcs will be seen twice, providing excellent surface mapping coordinates, if desired.

The arrows in FIG. 3 showing rotation indicate what happens if the inspector rotates the wire or other test object around its axis (i.e., rotation toward or away from the inspector's line of sight). If the rotation is counter-clockwise, i.e., such as to bring A toward, and B away from the line of sight, the inspector will then see both images rotate in a clockwise direction, i.e., A' will move away, and B' toward the inspector. Although this may be visually confusing at first, the viewing technique may be learned quickly: if one sees a flaw in any one (or two) of the three views, it becomes perfectly natural to slightly rotate the wire or other test object to bring one of the images into the center of one of the fields of view. With computer-assisted television viewing, on the other hand, such corrections for visual satisfaction are unnecessary, since the geometrical mapping information from the three overlap arcs is more than sufficient to pin-point and delineate any flaws seen.

It is also noted that the virtual objects seen in the upper and lower reflected rear views are, by geometrical optics, located farther from the eye or viewing camera lens than is the direct view of the target surface. Consequently, the images of the upper and lower rear views formed on a camera CCD or on the eye's retina are smaller in all dimensions than is the image of the direct view. However, this scaling factor is exactly calculable by geometry once the optomechanical design of the double-mirror system with respect to the viewing lens (e.g., eye, TV camera or IR camera) is fixed. The effect of this scaling factor is also illustrated in FIG. 3—the rear view section images appear to be shorter and thinner than the direct view. The locations of the reflected off-axis points A' and C' are also shifted from strict Cartesian geometry, but these shifts are not to be confused with barrel distortion. This optical effect has no influence on the accuracy or reliability of mapping defects on the test surface, since the scaling factor can be built into the image analysis software for automatic image size compensation in a manner known to those of ordinary skill in the pertinent art.

Figure 4:
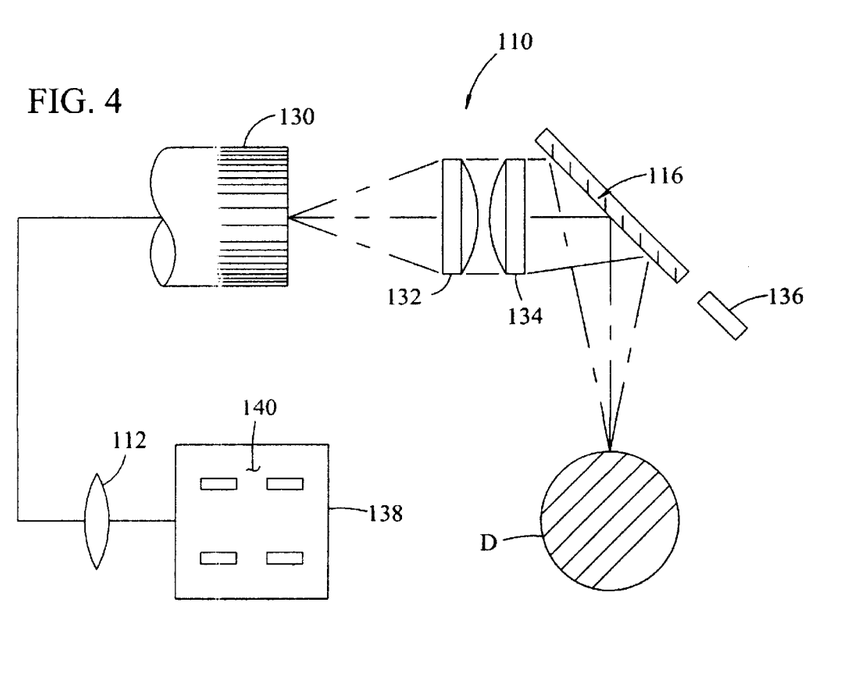
FIG. 4 is a schematic illustration of a second embodiment of the invention employing fiber-optic image conduits and a miniature visible-range camera for simultaneously viewing at least three, spatially distinct images forming a 360° view of a target surface.
Figures 5, 6:
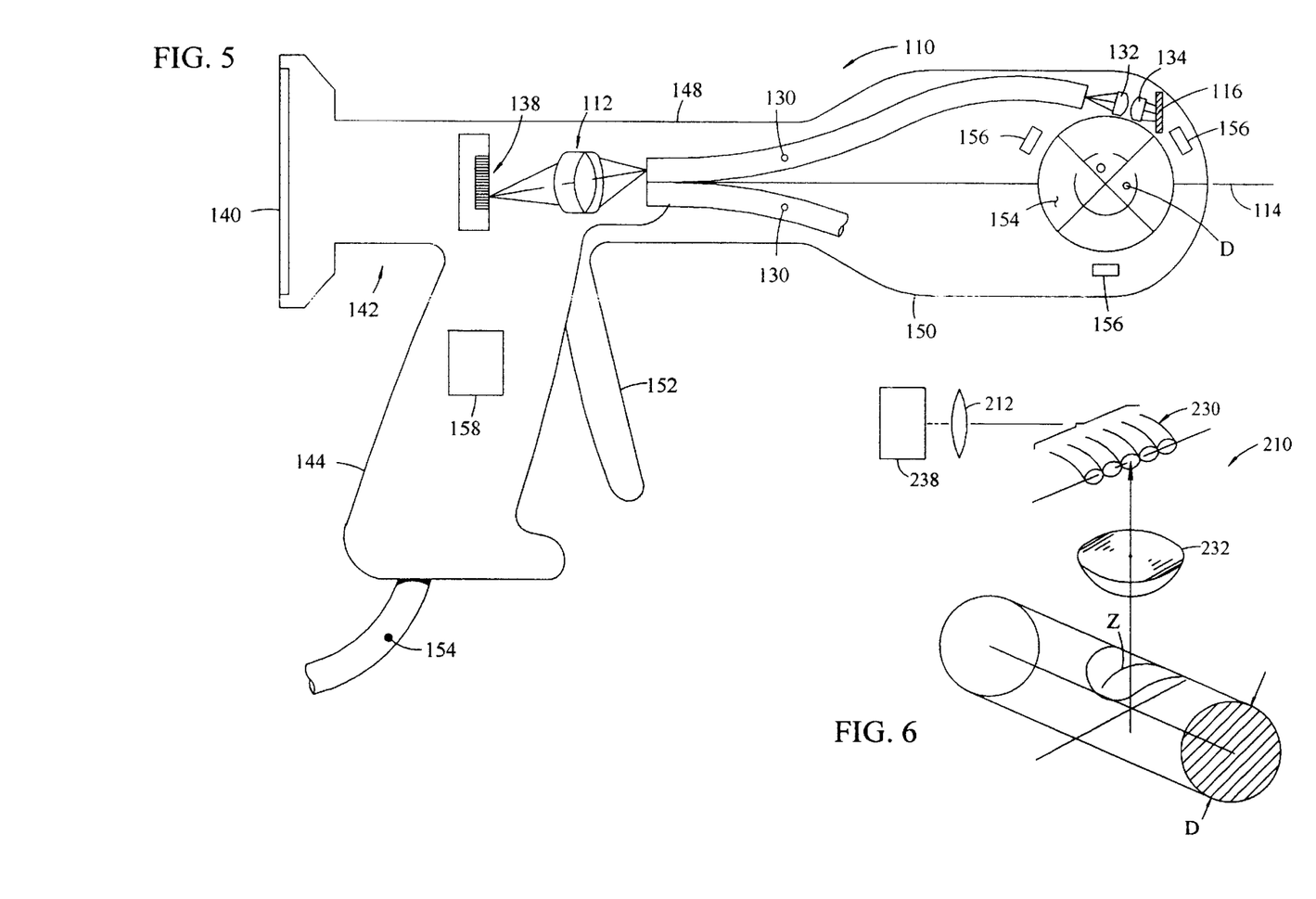
FIG. 5 is a schematic illustration of the apparatus of FIG. 4 mounted within a hand-held instrument for scanning cables, wires or like test objects for visual inspection.
FIG. 6 is a partial, schematic illustration of another embodiment of the invention employing diffuse reflection measurement of the target surface.

In FIGS. 4 and 5, another apparatus embodying the present invention is indicated generally by the reference numeral 110. The apparatus 110 is the same in many respects as the apparatus 10 described above, and therefore like reference numerals preceded by the numeral 1 are used to indicate like elements. The primary difference of the apparatus 110 is that fiber-optic image conduits and a miniature TV camera are used to simultaneously observe, for example, four views of an insulated wire, harness, or other test object.

As shown typically in FIG. 4, the apparatus 110 includes a plurality of fiber-optic image conduits 130, each optically coupled through a respective pair of first and second relay micro-lenses 132 and 134, respectively, to a respective surface plane mirror, shown typically at 116. Ultra-bright red LEDs 136 are mounted on either side of each mirror for laterally-illuminating the viewed area. In the preferred embodiment, the apparatus 110 comprises four image sensors (each sensor includes the mirror shown typically at 116, micro-lens pair 132, 134, and ultra-bright LEDs 136), four fiber-optic image conduits 130, a common CCD image receiver 138 optically coupled to the four image conduits 130, and a display screen 140 coupled to the receiver for simultaneously displaying the four images of the test or target surface. In the embodiment of the present invention illustrated, each fiber-optic conduit is a 3.2 mm, 60 line/mm conduit; however, as will be recognized by those skilled in the art, a different number of imaging sensors, as well as numerous other types fiber-optic cables and optical coupling devices equally may be employed.

In FIG. 5, the apparatus 110 is shown in the form of a hand-held instrument configured much like a soldering or caulking gun in the manner described above with reference to the embodiment of FIG. 1. The hand-held instrument 110 comprises a frame 142 including a handle 144, an eyepiece 146 containing the miniature display screen 140, and an upper jaw or arm 148 projecting outwardly from the handle. A lower jaw or arm 150 is hingedly (or pivotally) connected to the upper jaw 148 at the fulcrum "X", and a trigger 152 is fixedly secured to the lower jaw. As shown in FIG. 5, each of the upper and lower jaws 148 and 150, respectively, defines a recess adjacent to its distal end, and the two recesses form a test aperture 154 for receiving the wire or other test object between the jaws. The optical axis 114 of the instrument extends through the test aperture 154, and the origin "0" is located within the center of the aperture. As also shown typically in FIG. 5, two fiber-optic image conduits 130 and their associated image sensors are fixedly mounted within the upper jaw 148, two fiber-optic image conduits 130 and their associated image sensors are fixedly mounted within the lower jaw 150, and each of the four mirrors 116 is angularly spaced approximately 90° relative to the next for simultaneously generating four, equi-angular views of the test surface. A receiving or high-quality relay lens 112 is mounted within the frame 142 and is optically coupled to the other ends of the fiber-optic image conduits 130 with its center aligned with the optical axis 114 and origin "0" of the instrument. A board-level CCD 138 having a mosaic monochrome detector, is also mounted within the frame 142 and optically coupled between the relay lens and the miniature display 140 (e.g., an LCD display) for simultaneously transmitting and displaying the four equi-angular views of the test surface. An electronic umbilical cord 154 is mounted through the base of the handle 144 and contains a power line and other suitable connectors for powering the electronic components of the instrument and/or for connecting the instrument to a computer, if desired.

The trigger 152 and lower jaw 150 are spring-loaded in a manner known to those of ordinary skill in the pertinent art so that the lower jaw is normally biased into the closed position in contact with the upper jaw. However, in operation, the trigger 152 may be depressed against the bias of the spring (not shown) to open the jaws and receive the wire or other test object over the origin "0" of the instrument. The trigger then may be released to close the jaws around the test object without necessarily contacting the object. The instrument then may be moved slowly by hand (i.e., "scanned") along the wire or other test object until an obstruction prevents further travel or the entire object is scanned. Each upper image conduit, shown typically at 130 in FIG. 5, is a gently-bent, rigid conduit with its exit (or left) end mounted in a fixed position immediately in front of the instrument fulcrum at the "X" location. The upper conduits 130 are neither touched nor otherwise disturbed by movement of the lower jaw (or arm) 150 between its open and closed positions. Light emerging from the left end of the first upper conduit 130 is focused without any further loss of resolution onto a lower quadrant of the CCD 138. Light from the companion upper image conduit 130 (not shown) is transmitted onto the other lower quadrant of the CCD 138, thereby placing the two upper views of the wire or other test object side-by-side on the CCD, simultaneously. The two lower image conduits 130 (only one shown) are gently bent in the same manner as the upper conduits, and rigidly attached to the lower jaw or arm 150. Only when the lower jaw 150 is in the closed position surrounding the test object will the exit (or left) ends of the lower image conduits 130 be in the proper position to have their two light beams in sharp focus on the two upper quadrants of the CCD 138. When this is the case, however, the inspector will see within the display 140 all four images, side-by-side, each in a respective quadrant of the display, constituting a 360° or circumferential view of the wire or other test object. The inspector may move the handle or grip 144 slightly by his or her own hand motion to get any one of these images in as sharp focus as possible.

In order to assist the inspector in maintaining the wire or other test object optimally centered in the test aperture 154 at all times (even during "scanning" as the instrument is moved along the length of the test object), the use of an ultrasonic triangulation sensor may be employed. The triangulation sensor comprises three miniature, high-frequency electret microphones/sensors 156 mounted on the upper and lower jaws 148 and 150, respectively, adjacent to the test aperture 154, and angularly spaced approximately 120° relative to each other. When pulsed, each sensor 156 generates a 10 $\mu$sec or shorter ultrasonic pulse, and for a beeper-to-wire distance of about 5 mm, for example, the round trip time for the leading edge of the pulse is about 30 $\mu$sec, thus permitting distance ranging by each sensor. The three measured time delays from the sensors 156 are transmitted to a logic circuit 158, which may be mounted, for example, in the handle 144 of the instrument, and the logic circuit compares each signal to the other. If there are any differences in the three signals, the logic circuit 158 produces an audio tone which only goes lower in pitch as all three time delays approach equality. Thus, the inspector may move his hand about, "hunting" almost subconsciously, to always keep the audio tone as low as possible. One advantage of the ultrasonic triangulation sensor is that the centering signal or "prompter" is entirely audible, and therefore does not in any way interfere with the inspector's operation and viewing of the instrument and its image display.

The fiber-optic design of FIGS. 4 and 5 should have a practical overall resolution at the LCD display 140 of about 2 mils (approximately 50$\mu$), inclusive of all sources of resolution loss. This resolution is sufficient to estimate, for example, crack depth in the target surface by assessing the relative darkness of the crack, i.e., the darker the image, the deeper the crack. In practice, when the inspector sees a relatively darker image on the LCD display 140, he or she will (typically as a reflex reaction) move his or her hand and the instrument around so as to sharpen the particular quadrant's image, which may in turn bring the resolution closer to the 60 line/mm level (approximately 0.7 mils) claimed by typical image conduit specifications. This level of resolution will enable the inspector to nearly quantitatively measure the dimensions of the defect or anomaly.

Figure 7:
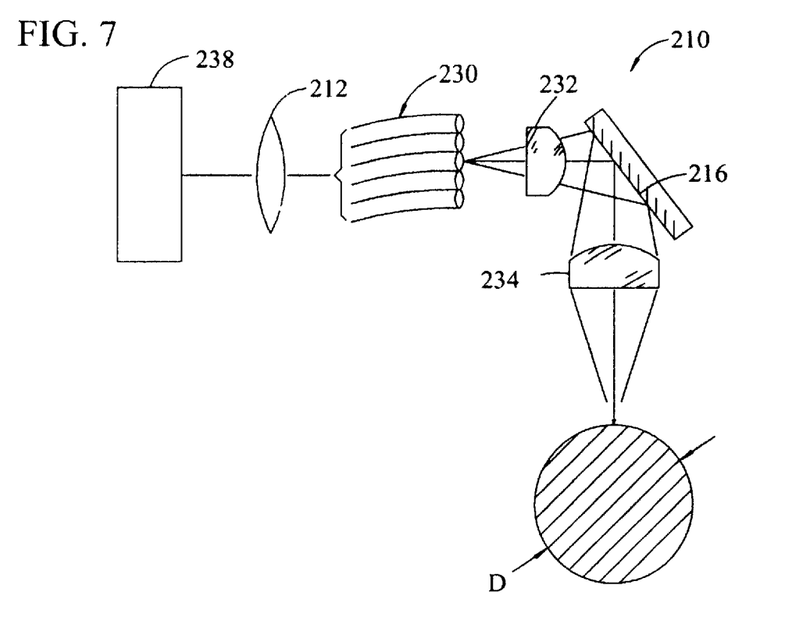
FIG. 7 is a partial, schematic illustration of an alternative to the embodiment of FIG. 6 employing surface mirrors and micro-lens pairs to provide sharper sensing of reflectance changes along the target surface.
Figure 8:
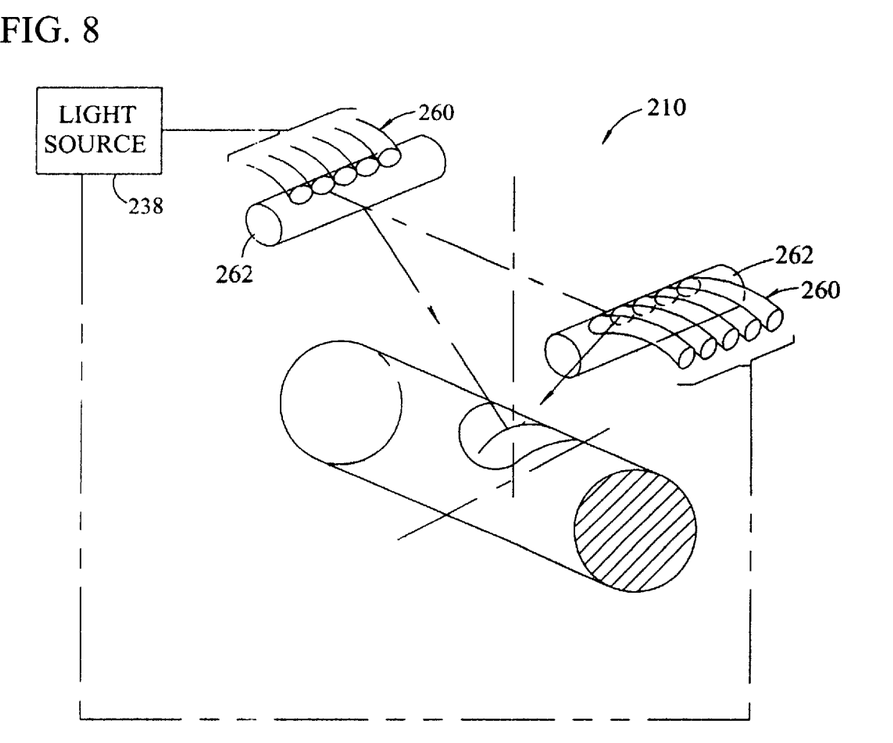
FIG. 8 is a partial, schematic illustration of the means provided for laterally-illuminating the target surface area with the diffuse-reflection configurations of FIGS. 6 and 7.
Figure 9:
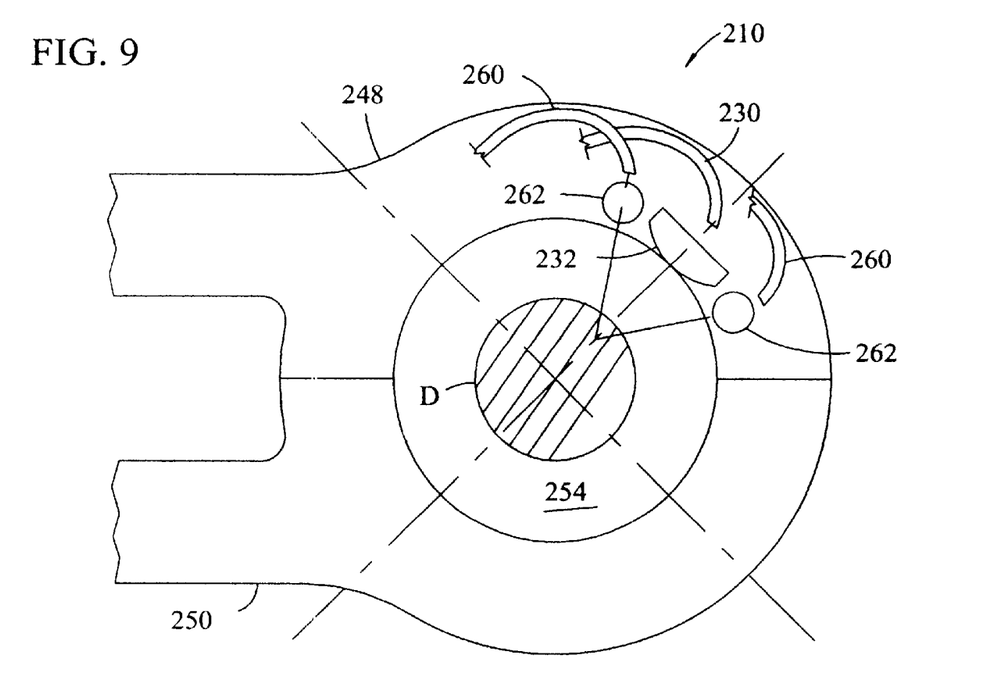
FIG. 9 is a partial, schematic illustration of the apparatus of FIGS. 6–8 mounted within a hand-held instrument.

In FIGS. 6–9, another embodiment of the present invention is indicated generally by the reference number 210. The apparatus 210 is similar in many respects to the apparatus 110 described above, and therefore like reference numerals preceded by the numeral 2 instead of the numeral 1 are used to indicate like elements. The primary difference of the apparatus 210 in comparison to the embodiments described above, is that this apparatus does not visually image the target surface, but rather makes a diffuse reflection measurement of the target surface during a scan. Accordingly, rather than sense image information in the manner described above, the apparatus 210 senses abrupt changes in signal level from point to point as the instrument (as shown in FIG. 9) is scanned along the target surface. As will be recognized by those skilled in the pertinent art, in order to ensure reliability, diffuse reflection inspection will require that the test surface be wiped reasonably clean, or be at least uniformly smeared.

FIGS. 6 and 7 illustrate typical linear fiber optic array configurations of the apparatus 210 for sensing an illuminated patch of a wire or other test object having a diameter "D", and which may have a typical stress crack "Z" in the insulative coating of the wire or like object (FIG. 6). As indicated in FIG. 9, the preferred hand-held instrument of the invention comprises at least three fiber-optic arrays and associated optical components (also referred to as "modules") equally spaced relative to each other about the origin "0" of the instrument for generating at least three side-by-side, non-vignetting images constituting a 360° view of the target surface. In FIG. 6, the linear fiber-optic array 230 preferably comprises a plurality of relatively low-cost plastic fibers, typically about 10 mil in diameter, and having a minimum bend radius of about ¼ inch. A respective micro-lens 232 is mounted between each fiber-optic array 230 and the target surface in order to focus the array on the surface. Each micro-lens 232 typically has a diameter of 3 mm or less, and a working distance of a few mm in each conjugate. A respective phototransistor 238 is optically coupled to the other end of each fiber optic array 230 and generates signals indicative of changes in the diffuse reflection from point to point on the target surface.

In FIG. 7, an alternative array configuration comprises a surface mirror 216, and respective first and second microlenses 232, 234 (Ramsden or Lister design) for improving imaging quality over the embodiment of FIG. 6. The arrangement of the micro-lens pair 232, 234 and the surface mirror 216 will provide sharper sensing of the reflectance changes along the target surface, and also ease the problem of bending the fibers within the confines of a small hand-held instrument.

In FIG. 8, the preferred construction for laterally illuminating the target surface comprises a pair of fiber-optic arrays 260, each optically coupled to a respective glass rod 262 forming a cylindrical lens for focusing the light emitted by the arrays onto the target surface. As shown schematically in FIG. 9, the array configurations of either FIG. 6 or FIG. 7 are mounted between the opposing glass rods 262 and fiber-optic arrays 260 to form a respective module for illuminating and imaging a respective section of the target surface. In the embodiment of the present invention illustrated, the glass rods 262 are preferably about 2 mm in diameter and function as cylindrical lenses, and the emitting ends of the fiber-optic arrays 260 are each spaced about 1 mm from the respective rear cylinder surface in order to have the best "focus" at the target surface. The aberrations will be relatively large, however, this is useful in smearing the illumination over a reasonably large patch of target surface.

Although in FIG. 9 only one of the imaging modules is illustrated, three additional modules are mounted within the upper and lower jaws 248 and 250, respectively, each spaced approximately 90° relative to the next, as indicated by the broken lines. The diameter and focal length of each micro-lens 232 (or of each micro-lens in the pair 232, 234) is selected to adequately cover the thickest wire or like test object (or the smallest) for which the instrument is designed. For example, in the inspection of wires or cables, one instrument might be designed for relatively thick wires, and another for relatively thin wires. Each hand-held instrument is connectable by an electrical umbilical cord (not shown) in the manner described above with reference to FIG. 5 to common electronics, a computer and read-out, with two or more plug-in instruments depending upon the size of the target to be inspected.

The handle (not shown) of the instrument 210 comprises either a plurality of ultrabright LEDs or semiconductor lasers (not shown) optically coupled to the input ends of the fiber-optic arrays 260 for illuminating the arrays. In the embodiment of the present invention illustrated, the apparatus comprises four or eight LEDs, depending upon the illumination brightness needed. Each of the four modules is illuminated at a different frequency (e.g., 500, 800, 1100 and 1400 Hz) so that there is no cross-talk between viewing channels by reason of any inter-reflections within the instrument. The handle of the instrument 210 also comprises four phototransistors 238 (not shown in FIG. 9) for detecting the reflected light transmitted by the four modules. Op-amp circuits (not shown) of a type known to those of ordinary skill in the pertinent art are also mounted within the handle to amplify and frequency-discriminate the signals from the different modules. In the preferred embodiment, the laser/LED sources will deliver about 1 milliwatt to each module, and therefore the optical signal reaching each phototransistor 238 will be greater than about 50 nanowatts. Accordingly, conventional IC components may be employed to amplify the signal into the millivolt range.

As will be recognized by those skilled in the pertinent art, the various embodiments of the invention described above may be easily modified for conducting infrared inspection of a wire, cable or other target surface (hereinafter referred to as the "infrared inspection embodiment"). The application of a steady current to a metal wire (or other electrically-conductive test object) having an insulative coating causes resistive heat to flow outwards and radiate away from the insulation's surface. Any sufficiently prominent flaw in the insulation, external or internal, which has an effective thermal conductivity different than that of the insulative coating, or which causes the effective path length from wire to surface to differ appreciably from the average value, will cause the steady-state surface temperature of the wire insulation to depart from its average value. Viewing the surface of such a heating wire (or other test object) with an infrared (IR) framing camera of sufficient sensitivity will allow direct observation of such flaws, and provide information which can be used to estimate the spatial extent of the flaw.

Accordingly, in each of the embodiments described above, the inspector's eye, or the visible-range camera may be replaced with an IR camera, and the IR camera may be coupled to a display, preferably an on-board color or black-and-white video screen. The three (or four) views of the target surface are displayed on the video screen; however, it is the temperature differences from the average which are seen by the inspector. Electric currents needed to produce sufficient heat flow will depend on the wire gauge (or test object thickness), and will generally be near the upper limit of the safe current handling range for each gauge. For example, the allowable current for rubber-insulated 14 gauge flexible copper wire is about 15 amperes (which is the most conservative rating for a variety of insulation materials). To avoid overheating the insulation, it is necessary to set the current level within the specified current-carrying limits, and therefore the IR camera should have a relatively high absolute and differential temperature sensitivity. Such cameras, viewing in the 2–5 $\mu$m or 8–12 $\mu$m atmospheric windows, are readily available, with temperature sensitivities of 0.1° C. at ordinary body temperatures. The portions of this detailed description above describing image redundancy, scanning inversion, and geometry with respect to the other embodiments are equally applicable to this infrared inspection embodiment.

In the operation of the infrared inspection embodiment, a stress crack emanating from the surface of wire insulation inwards (or from another target surface) will appear hotter than the average surface, since the IR camera is effectively seeing into a hotter region of the insulation. Similarly, a region of the target surface which has had the insulation abraded or chipped away will appear hotter than the average, since the insulation is thinner at this point than the average value, and therefore presents less of a barrier to outward heat flow. A delamination of the insulation emanating from the wire, on the other hand, may give the appearance of a cooler spot on the surface, since the internal delamination generally acts as a barrier to outward heat flow.

In the infrared inspection mode, it also may be desirable to externally heat the wire, cable or other test object, rather than employing steady-state electrical heating, as described above. One advantage of external heating is that electrical hook-ups and/or multi-ampere power supplies to the wire or other test object are not required. However, one disadvantage of external heating for purposes of wire inspection is that insulation flaws very close to the wire may not be accurately sensed. In addition, either dynamic heating/cooling or active scanning along the wire, rather than steady-state external heating, must generally be used. Nevertheless, the convenience of external radiant heating in an inspection method that utilizes scanning along the wire or other test object may overcome these drawbacks and render this a desirable approach under various circumstances.

Figure 10:
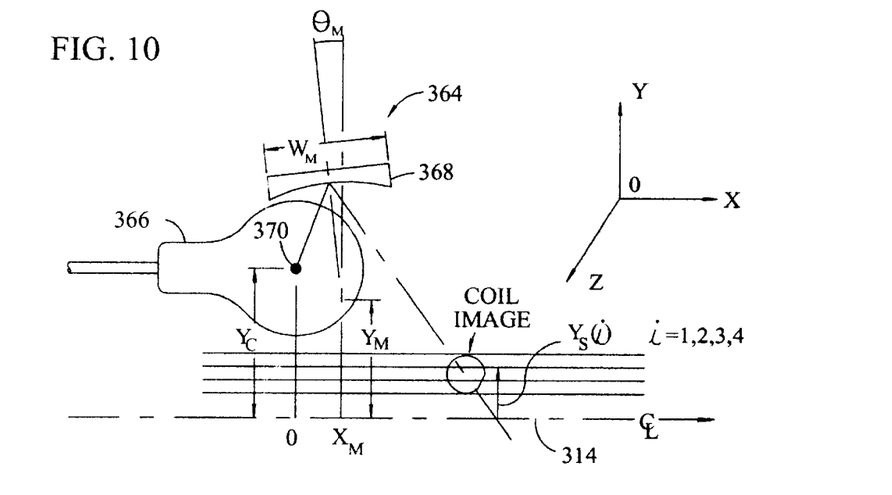
FIG. 10 is a partial, schematic illustration of a lamp/mirror arrangement employed in another embodiment of the invention for externally heating, and for conducting infrared inspection of the target surface.

In FIG. 10, a typical lamp/mirror assembly used for radiant heating of a straight wire section (at least over a few centimeters) is schematically illustrated in the meridional plane and indicated generally by the reference numeral 364. Each lamp/mirror assembly 364 is mounted within an instrument, preferably of the types illustrated in FIGS. 1–5, in the manner described above, i.e., with the inspector's eye, or the visible-range camera replaced with an IR camera, and the IR camera coupled to a suitable display, such an on-board color or black-and-white video screen. The preferred apparatus comprises three miniature tungsten lamps 366 (only one shown) fixedly mounted approximately 120° relative to each other about the center of the wire (or the origin "0" of the apparatus). Three relatively small, first-surface, off-axis, spherical mirrors 368 (only one shown) are each mounted adjacent to a respective lamp 366 and positioned to transfer visible radiation emitted by the lamp coils 370 to the vicinity of the leftmost (or rightmost, if preferred) edge of the viewing region.

The axis of the wire (or other test object) coincides with the optical axis 314 of the apparatus, and as shown in FIG. 10, various wire (or other test object) radii $Y_S(I)$ (ranging from about 2 to 5 mm in this embodiment) are of interest. The miniature tungsten bulb 366 is mounted above the largest $Y_S(I)$ of interest, with its cylindrical coil 370 oriented into the plane of the Figure, and arranged for illuminating (and heating) the leftmost edge of the desired viewing region. The coordinates (x,y) of the center of the coil 370 are (0,$Y_C$). The small mirror 368 is mounted off-axis with its center of curvature at ($X_M$,$Y_M$), with a tilt angle $θ_M$ with respect to the normal to the optical axis 314. Light from the coil 370 which penetrates the bulb (e.g., all wavelengths from the UV to below about 4$μ$ for a quartz bulb) in the upward direction are focused to the right of the lamp into a magnified, relatively poor quality image of the coil located in the insulation or other target surface region of interest, as indicated in dashed lines in FIG. 10. Because of the mirror optics, all wavelengths (UV, visible, near IR) form the same coil image, and there are no chromatic aberrations.

The region of the target surface seen by the IR camera is selected to extend from the coil image further to the right in FIG. 10 on the order of 10 mm. An aperture stop (not shown) prevents the IR camera (or inspector's eye) from seeing either the lamps 366 or mirrors 368; only the region to the right of the rough coil image (indicated in dashed lines) is of interest. Downward rays from the coil, along with the long-wavelength IR rays emitted by the coil, which are absorbed by the lamp bulb and re-radiated in all directions, predominantly in the mid-IR, also contribute to heating the target surface.

For a static wire or like test object, turning on the lamps 366 causes a rapid heating of the coil image regions (indicated by the dashed lines in FIG. 10). A thermal diffusion wave moves within seconds to the right from the image region in the Figure, and it is during this time that insulation flaws—which generally act as barriers to heat flow—can be seen most reliably on the image display of the IR camera (not shown). Thus, for a given lamp wattage and optical geometry, there is an optimum scanning speed for moving the lamps relative to the wire or other target surface (or vice-versa) (i.e., so that the relative cold wire moves into the relatively hot coil image region). The optimum scanning speed equals and is opposite to the velocity of the thermal transient wave along the insulation or other target surface. That velocity, in turn, is a function of the IR camera's absolute and differential sensitivities. The present inventors have observed optimum scanning speeds of the order of one to a few mm/sec when total lamp power (all three lamps) is of the order of 50 watts. Reducing lamp power reduces this optimum scan speed. Increasing lamp power, on the other hand, can overheat the insulation (or other target surface) in the time it spends (several seconds) passing the lamps (or vice-versa).

Figure 11:
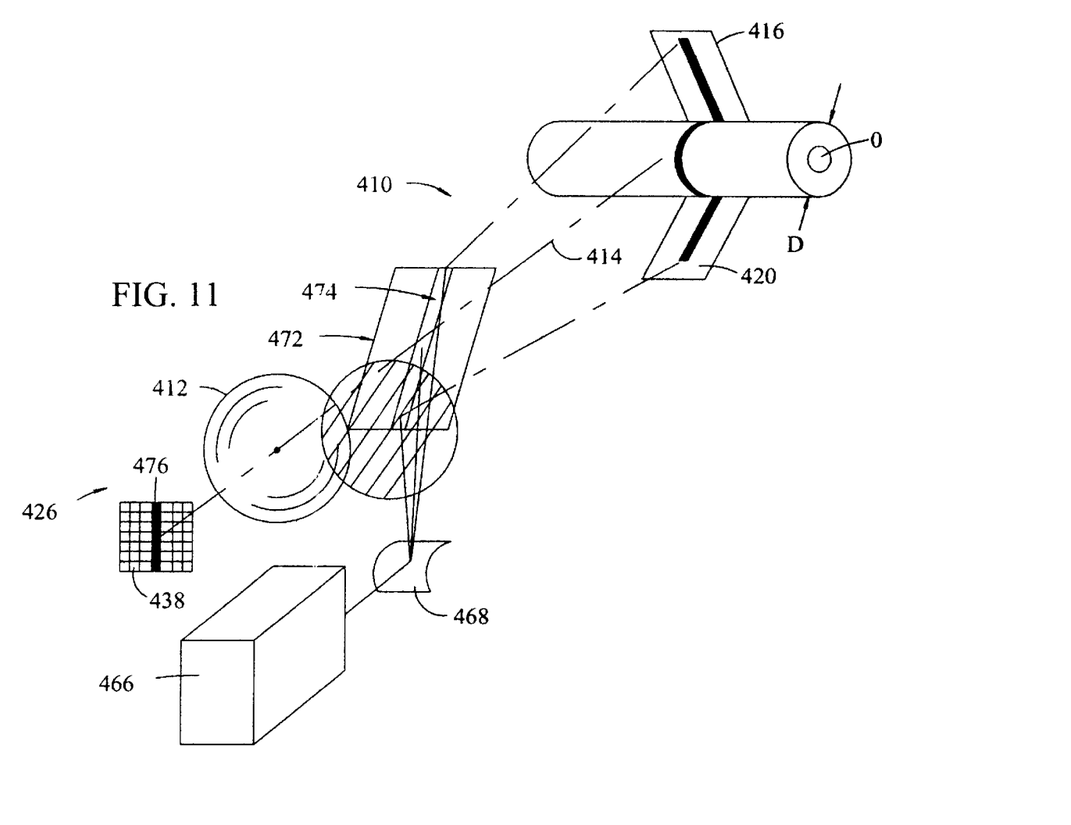
FIG. 11 is a schematic illustration of another embodiment of the invention employing a laser and auxiliary optics to heat, and in turn conduct infrared inspection of the target surface.

In FIG. 11, another apparatus embodying the present invention for conducting infrared inspection is indicated generally by the reference numeral 410. The apparatus 410 is similar in many respects to the apparatus 10 and 110 described above, and therefore like reference numerals preceded by the numeral "4", or preceded by the numeral "4" instead of the numeral "1", are used to indicate like elements. The primary difference of the apparatus 410 in comparison to the other infrared inspection embodiments described above, is that this embodiment employs a laser and appropriate auxiliary optics to form a circular band of radiant heat input around the circumference of the wire or other test object.

As shown in FIG. 11, the collimated output from a laser source 466 is reflected from a cylindrical metal mirror 468, which creates a vertical fan of radiation moving upwards to a 45° laser-blocking, IR-transparent plane mirror 472. The flat reflector 472 includes a laser-reflective strip 474, which in turn reflects the vertical fan of radiation onto the ±60° double-mirror configuration 416, 420. The fan of radiation is then further reflected by the ±60° double-mirror configuration 416, 420 to all sides of the target surface (having a diameter "D"). In the same manner as described above with reference to FIG. 2, the overlap of radiation in the A'A-type regions helps ensure roughly equal incident radiation levels on most of the circumferential arc. The heated circular band has a width approximating the original laser beam diameter, which is preferably on the order of about 1 mm.

Laser light scattered from the target surface is prevented from reaching the IR-lens 412 and CCD 438 of the IR camera 426 by the interference-coating design of the 45° plane reflector 472, which thus also serves as a blocking filter. A protective mask 476 also may be placed vertically in front of the camera's CCD 438 so that the central pixels will not accidentally be overloaded. The IR camera 426 thus sees the three views of the wire (or other test object) surfaces in the same manner as described above, but only to the right and left of the irradiated circular band. As the laser/IR camera/double-mirror system is moved along the wire (i.e., "scanned"), flaws or other imperfections entering the "hot zone" will be seen as they heat at a faster or (usually) slower rate than the average insulation (in the insulated wire scenario), and also may be seen as they leave the hot zone somewhere downstream from the irradiated circular band.

Figure 12:
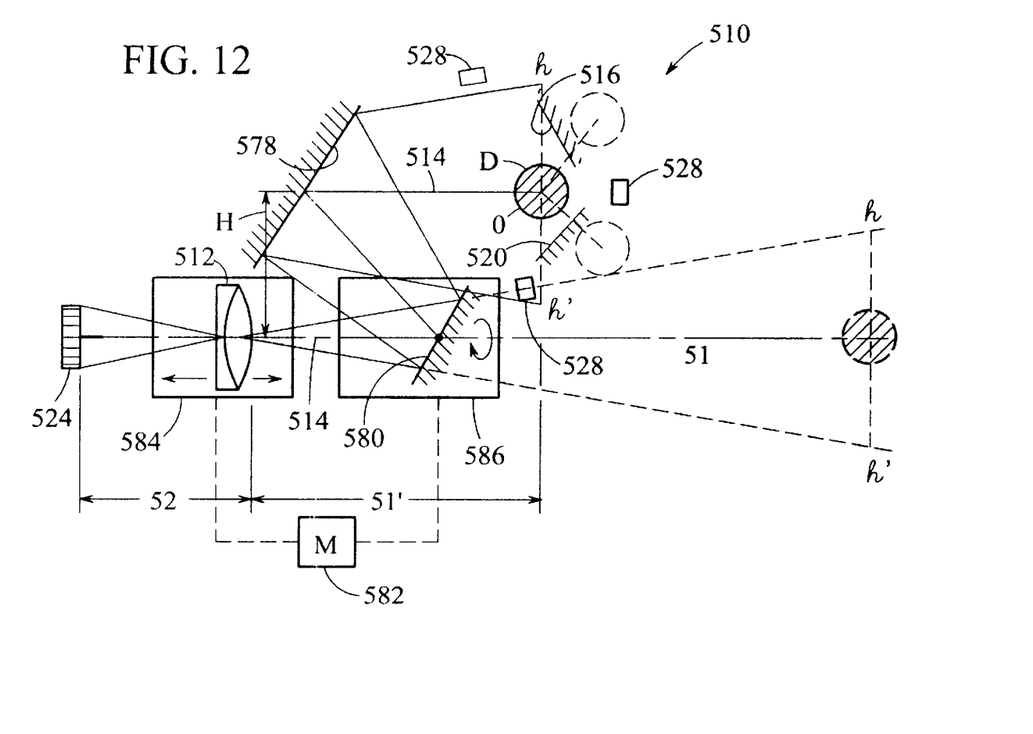
FIG. 12 is a partial schematic view of another embodiment of the invention employing a folded optical path in order to make the overall apparatus more compact.
Figure 13:
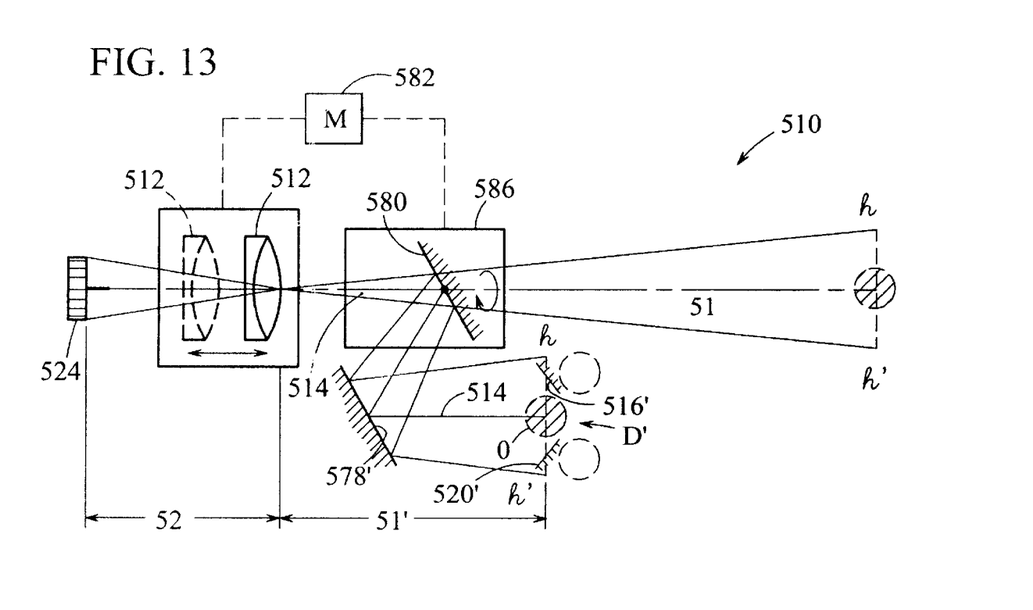
FIG. 13 is a partial schematic view of the apparatus of FIG. 12 showing the mirror 580 rotated 180° and the receiving lens 512 shifted relative to the positions of FIG. 12 in order to magnify the viewed images.

In FIGS. 12 and 13, another apparatus embodying the present invention is indicated generally by the reference numeral 510. The apparatus 510 is the same in many respects as the apparatus 10 described above with reference to FIGS. 1–3, and therefore like reference numerals preceded by the numeral "5" are used to indicate like elements. The primary difference of the apparatus 510 is that the optical path is folded in an approximately z-shaped pattern to make the overall apparatus more compact. In the currently preferred embodiment of the invention, the folding is accomplished by mounting two approximately parallel, first-surface flat mirrors, 578 and 580, optically coupled between the receiving lens 512 and first and second mirrors 516 and 520, respectively.

In FIG. 12, the wire or like target of a typical unfolded system (as shown, for example, in FIGS. 1–3) is illustrated in broken lines. As can be seen, in the unfolded system, the wire or like target is spaced a distance s1 straight across to the right of the receiving lens 512. In the currently preferred unfolded IR embodiment, the distance s1 is approximately 250 mm and the field of view is defined by the distance h–h'. In the folded system of FIG. 12, on the other hand, the wire or like target is spaced a distance "H" above the original optical axis (14,114), but much closer to the right of the receiving lens 512. In the illustrated embodiment, the distance H is approximately 60 mm, and the distance s1' between the plane of the origin "0" of the target and the receiving lens 512 is approximately 120 mm. Although in the folded embodiment the mirror 580 may slightly cut into the field of view h–h', as shown in FIG. 12, it does not interfere with any of the rays coming from the second mirror 520 and hence no vignetting occurs.

It may be desirable to magnify the images of the surface sections of the target to view, for example, relatively small diameter wires or like targets. The apparatus 510 of FIG. 12 defining the dimensions described above may be suitable for inspecting relatively large wires (e.g., up to 20 mm in diameter). In this type of apparatus, the images of the target surface sections on the CCD and viewing screen might be sufficiently large for inspecting wires as small as about 10 mm in diameter. However, for smaller wires or other target objects, it may be desirable to magnify the viewed images. Accordingly, the apparatus 510 further comprises means for moving at least one of the receiving lens 512 and the mirror 580 relative to each other along the optical axis, and means for rotating the mirror 580 about the optical axis. In the embodiment of FIGS. 12 and 13, this means includes at least one motor 582 drivingly connected to a translatable lens mount 584 and a rotatable mirror frame 586 upon which the mirror 580 is fixedly mounted. Also, as shown in FIG. 13, the apparatus 510 includes additional mirrors 516', 520' and 578' mounted below, or otherwise angularly spaced relative to the corresponding mirrors 516, 520 and 578 of FIG. 12. The mirrors 516', 520' and 578' are essentially the same as the corresponding mirrors of FIG. 12; however, as shown in FIG. 13, each mirror is spaced closer to the origin "0" than is the corresponding mirror of FIG. 12. In addition, as mentioned above, the receiving lens 512 in FIG. 13 is shifted closer to the plane of the origin "0" than in FIG. 12 in order to reduce the distance s1 in comparison to the distance s2, and in turn magnify the two-dimensional images of the target surface sections. As will be recognized by those skilled in the pertinent art based on the teachings herein, the positions of the mirrors relative to the origin "0" of the target may be adjusted as desired in order to set the desired magnification of the viewed surface section images. Although not shown, the apparatus 510 preferably includes separate apertures or slots for receiving the wires or like targets. The first aperture is larger in size than the second aperture, and is formed between the mirrors 516, 520 and 578 of FIG. 12 for receiving relatively larger diameter or larger sized wires or other test objects. The second aperture is smaller in size than the first aperture, and is formed between the mirrors 516', 520' and 578' of FIG. 13 for receiving relatively smaller diameter or smaller sized wires or other test objects. Accordingly, one advantage of the apparatus 510 of FIGS. 12 and 13 is that it is adapted to inspect a relatively broad range of test object diameters or other sizes.

The translatable lens mount 584 and rotatable mirror frame 586 each may take any of numerous different configurations currently, or which may later become known to those skilled in the pertinent art for performing the functions described herein. For example, the translatable lens mount 584 may include a carriage fixedly holding the receiving lens 512 and mounted by bearings or otherwise slidably mounted on a track or like means for moving the receiving lens between first and second, or any of a plurality of different lens positions. The carriage may be drivingly connected by any of numerous different gears or gear trains to the drive motor 582 for moving the lens into the desired positions. The rotatable mirror frame 586 likewise may be drivingly connected to the motor 582 by any of numerous different types of gears or gear trains in order to rotatably drive the mirror 580 about the optical axis 114. The motor 582 may be a small reversible DC motor geared to both rotate the mirror frame and shift the lens mount, or equally may take the form or configuration of any of numerous different motors which now or later become known to those skilled in the pertinent art. Alternatively, if desired, the motor or motors may be eliminated, and the translatable lens mount and rotatable mirror frame may be shifted and rotated, respectively, by manual manipulation.

As shown, the mirror 580 may be rotated approximately 180° about the optical axis 114, and the receiving lens 512 shifted along the optical axis, each from a first position of FIG. 12 into a second position of FIG. 13, for magnifying the viewed images and thereby facilitating visual inspection of relatively small diameter wires or other target surfaces (e.g., wires having diameters of 10 mm or less). By shifting the receiving lens 512 forward several millimeters, and thereby decreasing the distance s1' in comparison to the distance s2, the system's magnification is automatically increased such that a wire or like target having a diameter of about 8 mm will appear on the CCD's viewing screen to be about the same size as does a 20 mm target in the orientation of FIG. 12.

As will be recognized by those skilled in the pertinent art based on the teachings herein, the receiving lens 512 and/or mirror 580 each can be moved to any desired point along the optical axis 114 to achieve the desired folding of the optical path. When the mirror 580 and receiving lens 512 are closer toward each other, the mirror is necessarily oriented at a lesser angle (i.e., flatter) relative to the optical axis 114 in order to capture and reflect the entire bundle of image rays. In the limit, the mirror 580 can be oriented either nearly but not exactly parallel to the optical axis, or nearly but not exactly perpendicular to the optical axis. Depending upon the position and orientation of the mirror 580, the angular orientations of the other mirrors 578, 516 and 520 are adjusted accordingly to image the surfaces of the wire or like targets in accordance with the teachings herein.

Figure 14:
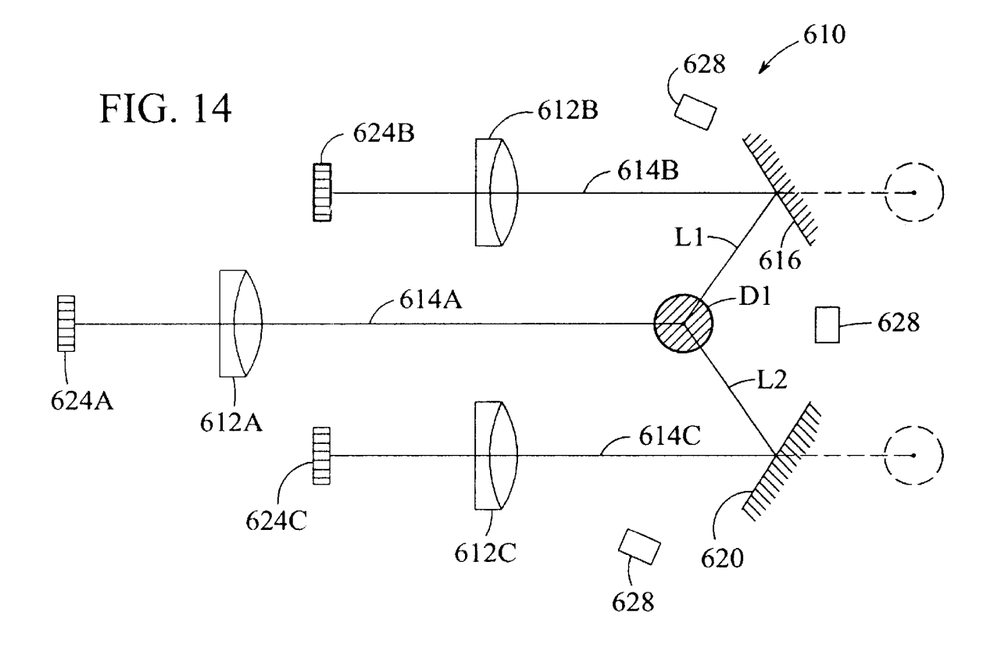
FIG. 14 is a schematic view of another embodiment of the invention employing separate receiving lens and detector pairs for generating images of the respective surface sections of the target surface.

In FIG. 14, another apparatus embodying the present invention is indicated generally by the reference numeral 610. The apparatus 610 is the same in many respects as the apparatus 10 and 510 described above, and therefore like reference numerals preceded by the numeral "6", or preceded by the numeral "6" instead of the numeral "5", are used to indicate like elements. The primary difference of the apparatus 610 is that instead of having a single receiving lens and associated image detector, the apparatus 610 comprises a plurality of receiving lenses, 612A–612C, and a plurality of associated image detectors 624A–624C, wherein each receiving lens and image detector pair receives and generates an image of a respective surface section of the wire or other target surface to thereby generate the image pattern forming the 360° view of the target surface area.

Although the use of a single image detector as described above is highly economical, it may not always be possible to have a sufficient depth of field to obtain the desired resolution on all three images. Accordingly, employing a plurality of image detectors in the manner indicated may overcome this problem. In addition, the plural detectors need not be TV-compatible 4:3 aspect ratio arrays, but rather may take the form, for example, of stripe arrays to more closely match the wire or other target images, and may transmit digital images directly to a CPU or like processor 658 for performing whatever type of image processing may be desired.

With reference to FIG. 14, the distances s and s' are related to f in the same manner as described above: $(1/s)+(1/s')=(1/f)$. As may be seen in FIG. 14, the first and second mirrors 616 and 620, respectively, may be spaced slightly further from the target than in the above-described embodiments to facilitate separate viewing of the upper right and lower right surface sections by the separate receiving lens and detector pairs.

Figure 15:
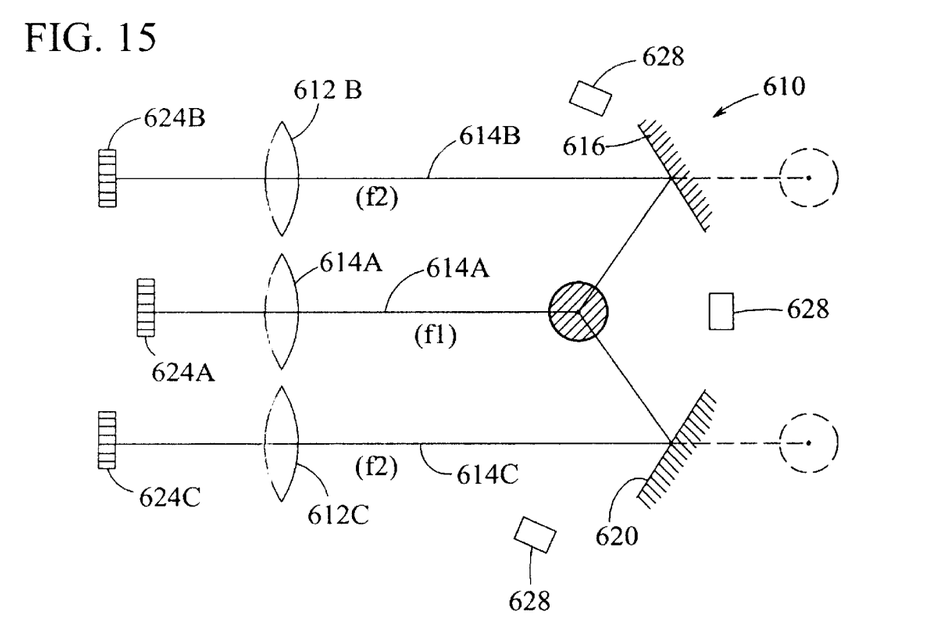
FIG. 15 is a schematic view of another embodiment of the invention employing a plurality of receiving lens and detector pairs, wherein the central receiving lens defines a relatively short focal length (f) in order to generate a plurality of distinct, non-vignetting images of approximately the same size.

FIG. 14 illustrates the arrangement of the lens and detector pairs when all focal lengths are the same, i.e., the distances s and s' are the same for each of the three "channels". If desired, however, and as shown in FIG. 15, the focal length (f1) of the central receiving lens 612A can be made shorter than that (f2) of the two outer receiving lenses, 612B and 612C, so that the three separate images may all be seen at the same magnification. In this configuration, the central detector 624A may require a smaller pitch than the outer two in order to obtain three apparently equal image sizes.

As will be recognized by those skilled in the pertinent art, numerous changes and modifications may be made to the above-described and other embodiments of the present invention without departing from its scope as defined in the appended claims. Accordingly, this detailed description of preferred embodiments is to be taken in an illustrative, as opposed to a limiting sense.

What is claimed is:

1. An apparatus for generating a 360° view of a surface area of a three-dimensional object and inspecting the surface area for flaws or imperfections, comprising:

first means defining a first field of view for generating a first, two-dimensional image of the first field of view corresponding to a front surface section of the object, wherein the first means defines an optical axis extending through the object, and an origin located on the optical axis within the object and spaced a first predetermined distance from the first means;

second means defining a second field of view for generating a second, two-dimensional image of the second field of view corresponding to a first rear surface section of the object, wherein the second means is spaced a second predetermined distance from the origin on another side of the object relative to the first means, and the second image is defined in part by a first central ray defining a first angle of incidence with respect to the second means;

third means defining a third field of view for generating a third, two-dimensional image of the third field of view corresponding to a second rear surface section of the object, wherein the third means is spaced a third predetermined distance from the origin on another side of the object relative to the first means, and on another side of the optical axis relative to the second means, and the third image is defined in part by a second central ray defining a second angle of incidence with respect the third means; and wherein the second and third predetermined distances and the first and second angles of incidence of the second and third means are each selected to simultaneously generate the first two-dimensional image of the front surface section, and the second and third two-dimensional images of the first and second rear surface sections in an image pattern forming a 360° view of the surface area.

2. An apparatus as defined in claim 1, wherein the second and third predetermined distances and the first and second angles of incidence of the second and third means are each further selected to simultaneously generate the first, second and third two-dimensional images in a non-vignetting image pattern.

3. An apparatus as defined in claim 1, wherein the first means comprises at least one receiving lens defining the first field of view, the second means comprises a first mirror defining the second field of view, and the third means comprises a second mirror defining the third field of view.

4. An apparatus as defined in claim 3, further comprising at least two approximately parallel mirrors optically coupled between the first and second mirrors and the receiving lens.

5. An apparatus as defined in claim 4, further comprising at least one of (i) means for rotating at least one of the two approximately parallel mirrors about an optical axis, and (ii) means for moving the at least one receiving lens along an optical axis.

6. An apparatus as defined in claim 3, comprising a plurality of receiving lenses, each receiving lens being optically coupled to one of the front surface section, first rear surface section, and second rear surface section, for receiving the two-dimensional image of the respective surface section.

7. An apparatus as defined in claim 6, wherein the receiving lens optically coupled to the front surface section defines a shorter focal length than at least one other receiving lens for generating a plurality of surface section images of approximately the same size.

8. An apparatus as defined in claim 1, further comprising means for viewing the first, second and third two-dimensional images, and wherein the second and third predetermined distances and the first and second angles of incidence are each further selected to simultaneously display on the viewing means the first, second and third two-dimensional images spaced relative to each other.

9. An apparatus as defined in claim 1, wherein the front surface section of the first image, the first rear surface section of the second image, and the second rear surface section of the third image, each overlap one another to thereby provide imaging redundancy from one image to the next.

10. An apparatus as defined in claim 1, wherein the first, second and third means each comprises at least one fiber-optic conduit optically coupled to the respective surface section of the object for generating the respective two-dimensional image of the surface section.

11. An apparatus as defined in claim 10, wherein at least one of the first, second and third means further comprises a relay lens optically coupled between the associated surface area and the at least one respective fiber-optic conduit for focusing the respective first, second or third image onto the at least one respective conduit.

12. An apparatus as defined in claim 1, further comprising means mounted laterally with respect to at least one of the second and third means for illuminating the surface area.

13. An apparatus as defined in claim 1, further comprising means optically coupled to the first, second and third means for detecting the first, second and third images and generating the at least three non-vignetting images.

14. An apparatus as defined in claim 1, wherein at least one of the first, second and third means comprises at least one fiber-optic conduit optically coupled to the respective surface section for generating the respective two-dimensional image, and the apparatus further comprises:

means focused toward the origin for illuminating the surface area; and at least one phototransistor optically coupled to the fiber-optic conduits for generating signals indicative of changes in the diffuse reflection of the surface area.

15. An apparatus as defined in claim 1, further comprising:

means for emitting infrared radiation from the surface area; and an infrared camera optically coupled to at least one of the first, second and third means and generating the three non-vignetting images formed by the infrared radiation emitted from the surface area.

16. An apparatus as defined in claim 1, further comprising:

a laser source transmitting a beam of radiation;

a reflector mounted on an opposite side of the test object relative to the second and third means, and optically coupled between the laser source and the second and third means for reflecting the beam of radiation onto the second and third means, and in turn onto the surface area of the object; and an infrared camera optically coupled to at least one of the first, second and third means and generating the three non-vignetting images formed by the infrared radiation reflected off the surface area of the object.

17. An apparatus as defined in claim 1, wherein the second and third predetermined distances between the origin and the second and third means, respectively, are each greater than or equal to a minimum value based on (i) the predetermined distance of the origin from the first means, (ii) a diameter of the first means, and (iii) a width of the test object in the plane of the optical axis, to thereby generate at least three distinct, non-vignetting images.

18. A method for generating a 360° view of a surface area of a three-dimensional object and inspecting the surface area for flaws or imperfections, comprising the following steps:

generating a first, two-dimensional image of a first field of view corresponding to a front surface section of the object;

generating a second two-dimensional image of a second field of view corresponding to a first rear surface section of the object;

generating a third two-dimensional mirror image of a third field of view corresponding to a second rear surface section of the object; and simultaneously displaying the first two-dimensional image of the front surface section, and second and third two-dimensional images of the first and second rear surface sections in an image pattern forming a 360° view of the surface area.

19. A method as defined in claim 18, further comprising the step of simultaneously displaying on a viewing screen the first two-dimensional image, the second two-dimensional image, and the third two-dimensional image in a spatially distinct manner relative to each other.

20. A method as defined in claim 18, further comprising the step of simultaneously generating the first two-dimensional image, the second two-dimensional image, and the third two-dimensional mirror image in a non-vignetting image pattern.

* * * * *